United States Patent
Donovan et al.

(10) Patent No.: US 9,176,144 B2
(45) Date of Patent: Nov. 3, 2015

(54) COSMETIC USE OF A PROTEIN BELONGING TO THE RIBONUCLEASE FAMILY

(75) Inventors: Mark Donovan, Berville (FR); Dominique Bernard, Paris (FR); Isabelle Castiel, Nice (FR); Veronique Chaussade, Paris (FR)

(73) Assignee: L'OREAL, Paris (FR)

( * ) Notice: Subject to any disclaimer, the term of this patent is extended or adjusted under 35 U.S.C. 154(b) by 1062 days.

(21) Appl. No.: 12/515,198

(22) PCT Filed: Nov. 16, 2007

(86) PCT No.: PCT/FR2007/001887
§ 371 (c)(1),
(2), (4) Date: Dec. 8, 2009

(87) PCT Pub. No.: WO2008/068422
PCT Pub. Date: Jun. 12, 2008

(65) Prior Publication Data
US 2010/0311666 A1    Dec. 9, 2010

Related U.S. Application Data

(60) Provisional application No. 60/874,257, filed on Dec. 12, 2006.

(30) Foreign Application Priority Data

Nov. 17, 2006  (FR) ..................... 06 54965

(51) Int. Cl.
| | |
|---|---|
| *G01N 33/53* | (2006.01) |
| *G01N 33/68* | (2006.01) |
| *A61K 8/60* | (2006.01) |
| *A61K 8/66* | (2006.01) |
| *A61Q 19/00* | (2006.01) |
| *A61Q 19/08* | (2006.01) |
| *C12N 5/071* | (2010.01) |
| *C12Q 1/68* | (2006.01) |
| *G01N 33/50* | (2006.01) |
| *A61K 38/46* | (2006.01) |

(52) U.S. Cl.
CPC ............ *G01N 33/6881* (2013.01); *A61K 8/606* (2013.01); *A61K 8/66* (2013.01); *A61K 38/465* (2013.01); *A61Q 19/007* (2013.01); *A61Q 19/08* (2013.01); *C12N 5/0629* (2013.01); *C12Q 1/6883* (2013.01); *C12Y 301/2601* (2013.01); *G01N 33/5082* (2013.01); *G01N 33/6893* (2013.01); *C12N 2501/70* (2013.01); *C12Q 2600/158* (2013.01); *G01N 2333/922* (2013.01); *G01N 2500/00* (2013.01); *G01N 2800/20* (2013.01)

(58) Field of Classification Search
CPC .... C07K 14/4723; C07K 7/08; C07K 14/435; A61K 9/0014; C12N 5/0629; C12Q 1/6883; C12Q 2600/158; C12Q 2600/112; C12Q 2600/118; C12Q 1/6876; G01N 33/6881; G01N 2333/922; G01N 33/5008; G01N 2800/20

See application file for complete search history.

(56) References Cited

U.S. PATENT DOCUMENTS

| | | |
|---|---|---|
| 2006/0014282 A1 | 1/2006 | Fortunel et al. |
| 2006/0171936 A1 | 8/2006 | Gueniche et al. |

FOREIGN PATENT DOCUMENTS

| | | |
|---|---|---|
| EP | 0 943 679 A1 | 9/1999 |
| EP | 1 600 501 A1 | 11/2005 |
| FR | 2 667 778 A1 | 4/1992 |
| FR | 2 908 784 A1 | 5/2008 |
| WO | WO 00/73452 A2 | 12/2000 |
| WO | WO 2004/028479 A2 | 4/2004 |
| WO | WO 2006/000992 A1 | 1/2006 |
| WO | WO 2006/037922 A1 | 4/2006 |

OTHER PUBLICATIONS

Osawa et al., Recent evidence for evolution of the genetic code, Microbiol Rev. (Mar. 1992) vol. 56(1): 229-264.*
Harder et al., Psoriatic Scales: A promising source for the isolation of human skin-derived antimicrobial proteins, J Leukoc Biol. (Apr. 2005), vol. 77(4):476-86.*
Sticherling et al., Abstract 104: Detection of RNase7 immunoreactivity in inflammatory skin diseases, J. of Invest. Dermatology, vol. 121, No. 1, (Jul. 2003).*
Harder et al. (RNase 7, a Novel Innate Immune Defense Antimicrobial Protein of Healthy Human Skin, The J. of Biol. Chem., vol. 277(48):46779-84 (Nov. 2002).*
Harder et al. (Th2 cytokines inhibit bacteria-induced human beta-defensin-2 expression in keratinocytes, P007, Arch Dermatol Res (2004) vol. 295:320-407.*

(Continued)

*Primary Examiner* — Jacob Cheu
(74) *Attorney, Agent, or Firm* — Oliff PLC

(57) ABSTRACT

The present invention relates to the use, in cosmetics and in therapeutics, of at least one antimicrobial protein belonging to the ribonuclease family, ribonuclease 7, or of polypeptides derived from said protein, notably as a marker for evaluating the condition of the epidermis. It further relates to the use of at least one polypeptide according to the invention, of at least one nucleic acid sequence coding for a polypeptide according to the invention, or of at least one agent that modulates the expression or the activity, notably biological, of said polypeptide or of its interaction with an element of the extracellular matrix, for the preparation of compositions intended for the prevention and/or treatment of skin disorders.

2 Claims, 1 Drawing Sheet

(56) References Cited

OTHER PUBLICATIONS

Chan et al. (Expression of Interleukin-4 in the Epidermis of Transgenic Mice Results in a Pruritic Inflammatory Skin Disease: An Experimental Animal Model to Study Atopic Dermatitis, J. of Investigative Dermatology, vol. 117(4): 977-983 (Oct. 2001).*
Rost, Twilight zone of protein sequence alignments, Protein Engineering, vol. 12(2): 84-94 (1999).*
GDS2382 Reference Series GSE5667 (NCBI GEO Dataset Browser, Atopic dermatitis (HG-U133B), Dataset GDS2382 Reference Series GSE5667, Gene: "RNASE7", series published Oct. 1, 2006, attached as pdf having 7 pages, also available at http://www.ncbi.nlm.nih.gov/sites/GDSbrowser?acc=GDS2382, last visited Feb. 25, 2014.*
Hanly et al., Review of Polyclonal Antibody Production Procedures in mammals and Poultry, ILAR vol. 37(3):93-118.*
Wang et al., Infection and Immunity, vol. 73(11):7216-7225 (Nov. 2005).*
Cho et al., "The ribonuclease a superfamily of mammals and birds: identifying new members and tracing evolutionary histories," *Genomics*, vol. 85, 2005, pp. 208-220.
Harder et al., "RNase 7, a Novel Innate Immune Defense Antimicrobial Protein of Healthy Human Skin," *The Journal of Biological Chemistry*, vol. 277, No. 48, Nov. 29, 2002, pp. 46779-46784.
Mehul et al., "Identification and Cloning of a New Calmodulin-like Protein from Human Epidermis," *The Journal of Biological Chemistry*, vol. 275, No. 17, Apr. 28, 2000, pp. 12841-12847.
"Health and Nutritional Properties of Probiotics in Food including Powder Milk with Live Lactic Acid Bacteria," Report of a joint FAO/WHO Consolation, Cordoba, Argentina, Oct. 1-4, 2001.
Lundstrom et al., "Stratum Corneum Chymotryptic Enzyme: A Proteinase Which May Be Generally Present in the Stratum Corneum and With a Possible Involvement in Desquamation," *Acta Derm Venereol*, vol. 71, 1991, pp. 471-474.
Sticherling et al., "Abstract 104: Detection of RNase 7 immunoreactivity in inflammatory skin diseases," *Journal of Investigative Dermatology*, vol. 121, No. 1, Jul. 23, 2003.
Harder et al., "Psoriatic scales: a promising source for the isolation of human skin-derived antimicrobial proteins," *Journal of Leukocyte Biology*, vol. 77, No. 4, Apr. 2005, pp. 476-486.
Haisch et al., "*Staphylococcus aureus* strongly induces mRNA of the antimicrobial protein RNase 7 and proinflammatory cytokines in the human keratinocyte cell line HaCaT," *Archives of Dermatological Research*, vol. 295, No. 8-9, Feb. 2004, p. 364.

* cited by examiner

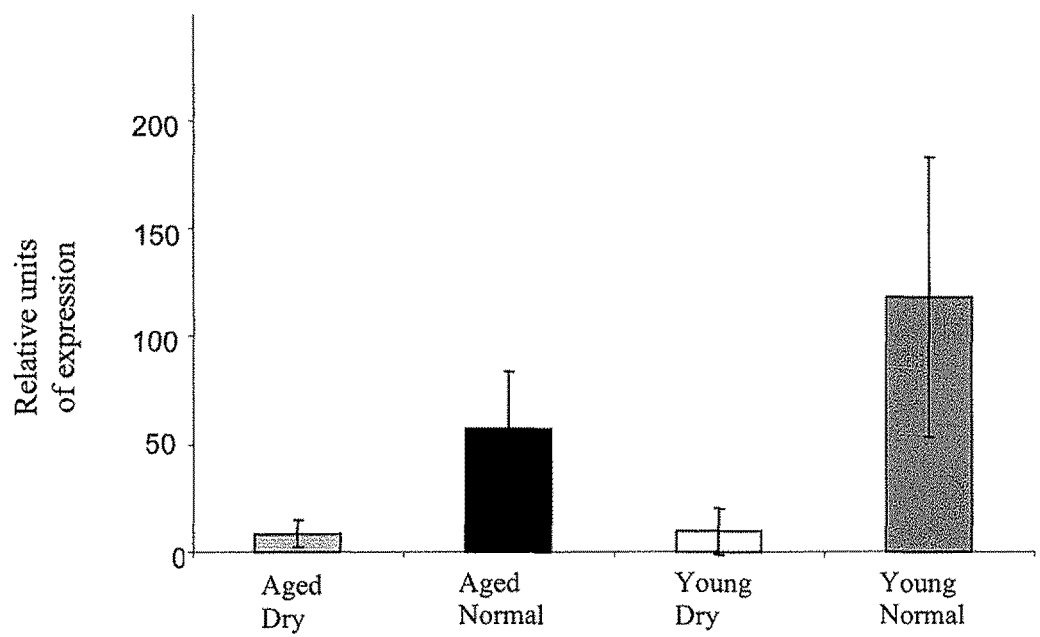

COSMETIC USE OF A PROTEIN BELONGING TO THE RIBONUCLEASE FAMILY

BACKGROUND OF THE INVENTION

Among its numerous physiological functions, the epidermis possesses the function of constituting a barrier that is at once biological, physical and chemical against the invasion of the organism by microorganisms.

The properties of the epidermis as a physical barrier are, notably, associated with its structural organization.

Thus, the epidermis is conventionally divided into a basal layer of keratinocytes constituting the stratum germinativum of the epidermis, the stratum spinosum constituted of several layers of polyhedral cells and finally a number of upper layers called cornified layers (or stratum corneum), constituted of keratinocytes at the final stage of their differentiation, called corneocytes.

The chemical barrier properties of the epidermis notably depend on the release, at the surface of the epidermis, of numerous antimicrobial proteins such as cathelicidins, the serine protease inhibitor antileukoprotease, dermcidin or proteins of the β-defensin family.

Numerous disorders or pathologies of the skin or of the scalp can result from dysfunction of the epidermal cellular structural organization, or from a defect in the chemical barrier function of the epidermis, such as dry skin, psoriasis, atopic dermatitis, ichthyosis, hyperkeratosis, inflammatory reactions resulting from microbial infections, or dandruff conditions.

To date, there are only a few biological markers for efficiently and accurately determining the condition of the epidermis, and notably for relating a disorder of the skin or of the scalp to a dysfunction of its physiological functions.

There is thus a need for biological markers that allow precise characterization of the condition of the epidermis.

There is also a need for a biological marker that could be used reliably in a method of diagnosis of a disorder of the skin or of the scalp.

There is also a need to identify new cosmetic or therapeutic targets in the epidermis.

There is also a need for new tools for screening molecules capable of exerting a cosmetic or therapeutic action on the epidermis or on keratinous materials in general. In the sense of the invention, the term "epidermis" will designate both the skin and the scalp.

There is also a need for new cosmetic or therapeutic compositions that can be used for the treatment of disorders of the skin or of the scalp resulting from the aforementioned dysfunction.

The present invention aims to meet all these needs.

BRIEF SUMMARY OF THE INVENTION

The present invention relates to the in cosmetics and in therapeutics, of at least one antimicrobial protein belonging to the ribonuclease family, ribonuclease 7, or of polypeptides derived from said protein, notably as a marker for evaluating the condition of the epidermis. It further relates to the use of at least one polypeptide according to the invention, of at least one nucleic acid sequence coding for a polypeptide according to the invention, or of at least one agent that modulates the expression or the activity, notably biological, of said polypeptide or of its interaction with an element of the extracellular matrix, for the preparation of compositions intended for the prevention and/or treatment of skin disorders.

DETAILED DESCRIPTION OF THE INVENTION

Thus, the present invention relates, according to one of its aspects, to the use of at least one polypeptide of amino acid sequence encoded by a nucleic acid sequence represented by all or part of a sequence represented by SEQ ID NO 1, an analog of the latter, or a fragment of the latter or of at least one nucleic acid sequence coding for said polypeptide, as a tool for evaluating the condition of the epidermis.

In particular, the evaluation can be carried out in vivo and more particularly in vitro or ex vivo.

According to another of its aspects, the present invention relates to the use of at least one polypeptide according to the invention, of at least one nucleic acid sequence coding for said polypeptide, or of at least one agent that modulates the expression or the activity of said polypeptide or its interaction with an element of the extracellular matrix for the preparation of a composition, notably cosmetic or therapeutic, intended for the prevention and/or treatment of a skin disorder.

In particular, a polypeptide, a nucleic acid sequence or a modulating agent according to the invention can be used as an active agent for improving the aesthetic appearance of the skin.

In the sense of the present invention, the expressions "modulating agent" or "chemical or biological compound capable of or suitable for modulating the biological activity and/or expression and/or interaction with an element of an extracellular matrix" means any compound capable of or suitable for acting, directly or indirectly, on at least one polypeptide according to the invention, a nucleic acid sequence coding for the latter, on an element of an intracellular or extracellular signalling pathway or of a metabolic pathway involving said polypeptide, on an element of the extracellular matrix, or on an element involved in the regulation of the transcription and/or translation of a nucleic acid sequence coding for said polypeptide.

Said modulating agents are described more particularly below.

According to another of its aspects, the present invention relates to the use of at least one polypeptide according to the invention, of at least one nucleic acid sequence coding for said polypeptide, or of a modulating agent as defined above for the preparation of a composition, notably cosmetic or therapeutic, intended for the prevention and/or treatment of a disorder of the scalp, for example a dandruff condition.

According to another of its aspects, the present invention relates to the use of at least one polypeptide according to the invention or of at least one nucleic acid sequence coding for said polypeptide, as tools for screening biological or chemical compounds or physical treatments that are able to modulate the biological activity and/or the expression of said polypeptide and/or its interaction with an element of the extracellular matrix and/or its interaction with another protein.

According to another of its aspects, the present invention relates to a method of assessing a condition of the epidermis comprising at least the steps consisting of:

a) determining a content of a polypeptide according to the invention or of nucleic acids coding for said polypeptide, in a sample of epidermis, and b) comparing said content determined in stage a) against a reference value.

The method can be carried out in vitro or ex vivo.

According to yet another of its aspects, the present invention relates to the use of at least one polypeptide according to the invention or of at least one nucleic acid sequence coding for said polypeptide or of at least one modulating agent as defined above, or of its interaction with an element of the extracellular matrix for the preparation of an isolated reconstructed skin.

In particular the present invention relates to a method of preparation of an isolated reconstructed skin comprising at least the step of contacting at least one polypeptide according to the invention, a nucleic acid sequence coding for said polypeptide, or at least one modulating agent as defined above, or of its interaction with an element of the extracellular matrix with cells capable of generating an isolated reconstructed skin, and notably keratinocytes.

According to yet another of its aspects, the present invention relates to a nontherapeutic method for demonstrating an effect of a treatment capable of causing regression of a skin disorder or for evaluating the effect of a cosmetic method for improving the condition of dry and/or aged skin in an individual. The method of evaluation notably comprises the steps consisting of:

a) carrying out, before the treatment and/or the application of the cosmetic method, at least one first determination, in a first sample of epidermis taken from said individual, of a biological activity and/or of the expression of a polypeptide according to the invention, b) carrying out, after the treatment and/or the application of the cosmetic method, at least one second determination, in a second sample of epidermis taken from said individual, of said biological activity and/or of said expression of the polypeptide determined in stage a), and c) comparer the first and second determinations, notably in order to deduce information therefrom concerning at least one effect of the treatment and/or the application of the cosmetic method.

In particular, the treatment whose effect is to be evaluated can be a treatment of a disorder of the skin or of the scalp associated with a dysfunction of proliferation and/or differentiation of the keratinocytes.

The uses and/or methods of the invention can more particularly be carried out in vitro and/or ex vivo.

According to another of its aspects, the present invention relates to a method of cosmetic treatment comprising at least one stage consisting of applying at least one cosmetic composition according to the invention on at least one part of the skin, the scalp, the mucosae and/or the keratin fibres.

According to another of its aspects, the present invention relates to the cosmetic use of at least one polypeptide according to the invention, of at least one nucleic acid sequence coding for said polypeptide, or of a modulating agent as defined above in a composition intended for the treatment and/or prevention and/or reduction of the skin signs associated with dry skin.

In the sense of the invention, the term "cosmetic" is to be understood according to the definition given in Directive 76/768/EEC, and in particular is intended to denote compositions or treatments intended for application on keratinous materials, for example the skin, the mucosae, the bristles and the hair, in order to clean them, perfume them, modify their appearance, notably aesthetic, and/or protect them or keep them in good condition.

Thus, the present invention is based more particularly on the identification, by the inventors, of ribonuclease 7 as an agent and/or a cosmetic or pharmaceutical target in the stratum corneum of the epidermis, as well as in the hair follicle.

In particular, this identification results from the unexpected observation according to which RNase 7 is expressed differentially in the stratum corneum of normal, young epidermis and of dry epidermis, in particular aged epidermis.

Thus, as can be seen from the examples presented below, the inventors determined the content of protein RNase 7, whose amino acid sequence is represented by the sequence SEQ ID NO 5, in the epidermis of young individuals and of older individuals, and notably of young nomnenopausal women and of older menopausal women. They observed, surprisingly, that the content of this protein was higher in the epidermis of the young women than in the epidermis of the older women, and was also higher in normally hydrated epidermis than in dry epidermis.

It is known that an increase in dryness of the skin is often observed with age, however such conditions of dry skin can also occur in young subjects. In fact, the condition of dry skin is a physiological condition that can occur in young subjects without any pathological cause, at least one that is evident. The origin of this dryness can be constitutional or acquired. Thus, numerous external factors can lead to drying out of the skin or can aggravate the condition of skin that is already dry. Among these factors we may mention harsh climatic conditions, solar radiation, exposure to certain chemical or therapeutic agents (for example the retinoids). This dryness is generally manifested by a sensation of tightness and/or tension. It is rough to the touch and appears covered with scales.

Unexpectedly, therefore, the inventors found that ribonuclease 7 constitutes a target for acting effectively on these skin disorders.

Ribonuclease 7 (RNase 7) is an endonuclease belonging to the ribonuclease family and, notably, the super-family A, which currently numbers thirteen members (Cho et al., Genomics, 2005, 85:208-220).

The ribonucleases are hydrolytic enzymes capable of cleaving nucleotide bonds.

In particular, RNase 7 displays antimicrobial activity.

Ribonuclease 7 was identified and localized by HARDER & SCHROEDER (J. Biol. Chem., 2002, 277: 46779-46784) in the stratum corneum of the epidermis and from primary cultures of keratinocytes. The latter also showed that this protein is endowed with antimicrobial properties.

RNase 7 is synthesized in the form of a proprotein of 156 amino acids (SEQ ID NO 4) containing a catalytic site of pancreatic ribonuclease type and a signal peptide of 28 amino acids at the N-terminal end (SEQ ID NO 6). Removal of the signal peptide leads to the generation of an active enzyme of 128 amino acids (protein SEQ ID NO 5).

In the sense of the present invention, unless stated otherwise, RNase 7 is intended to mean the proprotein form (SEQ ID NO 4), and the protein form (SEQ ID NO 5).

Polypeptide According to the Invention

According to one embodiment, a polypeptide suitable for the invention can have an amino acid sequence encoded by a nucleic acid sequence represented partly or completely by a sequence selected from SEQ ID NO 1, SEQ ID NO 2, or SEQ ID NO 3, or an analog of the latter, or a fragment of the latter.

According to another embodiment, a polypeptide suitable for the invention can have an amino acid sequence represented partly or completely by a sequence selected from SEQ ID NO 4, SEQ ID NO 5, SEQ ID NO 6, or SEQ ID NO 7, or an analog of the latter, or a fragment of the latter.

"Analog of a polypeptide" is intended to mean any polypeptide displaying a sequence homology, in particular with respect to one of the characteristic sequences of said polypeptide, as well as a biological activity of the same nature, carried for example by peptidomimetic sequences.

The homology can be at least 85%, for example at least 90%, and for example at least 95%. The homology can be determined by visual comparison or any information processing means generally used in this field.

The sequence homology can result from changes arising from mutations or from variations in the sequences of the peptides according to the invention resulting either from the deletion of one or more amino acids, or from the insertion of one or more amino acids, or alternatively from the substitution of one or more amino acids in the characteristic sequences of the polypeptides according to the invention.

"Characteristic sequence of the polypeptide" is intended to denote, notably with respect to RNase 7, the proprotein (SEQ ID NO 4), the active protein (SEQ ID NO 5), the signal peptide (SEQ ID NO 6), the active site comprising the amino acids in position 43 and 151, and comprising if applicable the amino acids surrounding these amino acids, at a rate, for example, of 1, or 2, or 3, or 4, or 5, or 6, or 7, or 8 amino acids on either side of the active site, the binding sites of the substrate represented by the sequence of amino acids 66 to 70 and the amino acid in position 91, and comprising if applicable the amino acids on either side of this binding site, at a rate, for example, of 1, or 2, or 4, or 8 amino acids on either side of these sites, as well as the sequence SEQ ID NO 7, representing an epitope derived from RNase 7.

Generally, the polypeptide analogs can include conservative substitutions relative to the amino acid sequence of the natural polypeptide.

Several of these modifications can be combined.

As an example of mutations that can be considered in the present invention, we may mention the replacement of one or more amino acid residues by amino acid residues having a similar hydropathic index though without having an appreciable effect on the biological properties of the polypeptide, and notably its biological activity such as its ribonuclease activity.

The hydropathic index is an index assigned to amino acids in relation to their hydrophobicity and their charge (Kyte and Doolittle (1982), J. Mol. Biol., 157: 105).

A polypeptide or analog also covered by the present invention can be a polypeptide that has undergone one or more posttranslational modification(s).

"Posttranslational modification(s)" is intended to encompass all the changes that a peptide or a protein can undergo at the end of its synthesis in a cell, for example phosphorylation or phosphorylations, glycosylation or glycosylations, lipidation or lipidations, such as a farnesylation or a palmitoylation, a structural rearrangement such as formation of disulphide bridges and/or cleavage within the peptide sequence.

The analog can, moreover, display roughly the same biological activity as the natural polypeptide.

According to one embodiment, a polypeptide suitable for application of the invention can also be a natural or synthetic polypeptide, if applicable obtainable after proteolysis of RNase 7 or by chemical or biological synthesis or by extraction from a biological tissue, for example the skin, expressing said polypeptide naturally or after transduction, as well as the various posttranslational forms of the latter, or alternatively any natural or synthetic polypeptide whose sequence comprises totally or partially (partly or completely) an aforementioned amino acid sequence, for example the variants and the analogs.

According to another embodiment, a polypeptide suitable for application of the invention can also be a polypeptide as defined previously fused with another polypeptide, a hydrophilic or hydrophobic targeting agent, a bioconversion precursor, a luminescent, radioactive or calorimetric labeling agent.

In a non-limiting manner, we may mention, as examples of compounds that can be coupled with a polypeptide according to the invention, fluorescent proteins such as the "Green Fluorescent Protein", fluorescent chemical compounds such as rhodamine, fluorescein, or Texas Red, phosphorescent compounds, radioactive elements, such as $^3$H, $^{35}$S, $^{121}$I or $^{125}$I, or calorimetric labeling agents such as chromogenic substrates sensitive to the action of galactosidase, of peroxidase, of chloramphenicol acetyltransferase, of luciferase or of alkaline phosphatase.

Depending on the nature of the compounds that can be coupled with a polypeptide according to the invention, coupling can be effected by chemical methods, notably by means of reactive chemical functions or by methods of molecular biology known by a person skilled in the art.

Nucleic Acid According to the Invention

In the sense of the present invention, "fragment of nucleic acid sequence" is intended to mean a nucleic acid sequence coding for all or part of a polypeptide according to the invention, an analog of the latter, or a fragment of the latter and in particular a nucleic acid sequence selected from SEQ ID NO 1 (coding for the proprotein form), SEQ ID NO 2 (coding for the active protein form), SEQ ID NO 3 (coding for the signal peptide), an analog of the latter, or a fragment of the latter.

"Analog of a nucleic acid sequence" is intended to mean any nucleic acid sequence, possibly resulting from the degeneration of the code of the nucleic acids, and coding for a sequence of a polypeptide identical or analogous to the sequence of the polypeptide encoded by said nucleic acid sequence.

A nucleic acid sequence according to the invention can be a sense, antisense or interference sequence corresponding to a sequence coding for a polypeptide according to the invention.

Thus, the present invention also relates to the use of nucleic acid sequences, notably of deoxyribonucleic acids, or of ribonucleic acids coding for a polypeptide according to the invention.

In this case, the invention also relates to the use of isolated and purified nucleic acid fragments encoding the claimed polypeptides.

The nucleic acid sequences according to the invention can notably be used for preparing sequences of corresponding, sense or antisense ribonucleic acids.

The invention also relates to the use of any polynucleotide, sense or antisense ribonucleic or deoxyribonucleic acid sequence, notably "small interfering RNA", corresponding at least to the nucleic acid sequence encoding SEQ ID NO: 1, SEQ ID NO: 2, or SEQ ID NO: 3 or an analog of the latter.

A nucleic acid sequence suitable for the invention can notably be as defined previously.

According to one embodiment, a nucleic acid sequence can represent a sense, antisense or interference nucleic acid sequence corresponding to said nucleic acid sequence coding for a polypeptide according to the invention.

The nucleic acid sequences can be derived from all possible origins namely either animal, in particular from mammals and even more particularly human, or vegetable, or from microorganisms (viruses, phages, bacteria among others) or alternatively from fungi, without prejudging whether or not they are present naturally in said source organism.

Method of Evaluation of the Condition of the Epidermis According to the Invention According to one embodiment, the present invention relates to a method of assessing a condition of the epidermis comprising at least the steps consisting of:

a) determining, in a sample of epidermis, a content of a polypeptide according to the invention, or of nucleic acids coding for said polypeptide, and b) comparing said content determined in stage a) against a reference value.

A method according to the invention can be carried out in vitro or ex vivo.

According to one embodiment, a method according to the invention can be carried out on a sample of epidermis taken from an individual.

A method according to the invention can also be carried out on a sample of epidermis taken from isolated reconstructed skin in order to assess its condition.

The determination of a condition of the epidermis may be indicative of a possible disorder of the skin or of the scalp. In particular a condition of the epidermis may be indicative of a possible skin disorder, notably selected from an excessive dryness of the epidermis, a xerosis, an ichthyosis, an atopy, an atopic dermatitis, a psoriasis, a hyperkeratosis, an eczema, an acne, a lichen, a pruritus, a rosacea, a seborrheic dermatitis, a palmoplantar keratoderma and a prurigo.

A method according to the invention can also be carried out on the scalp.

Methods of Sampling

A sample of epidermis can be obtained by any method known by a person skilled in the art.

These methods can be carried out by so-called stripping techniques.

These strippings are adhesive surfaces applied to the surface of the epidermis such as BLENDERM from 3M, D-SQUAME® (commercial adhesive from CuDERM), cyanoacrylate adhesive or the varnish stripping method. Using these strippings, the adherent corneocytes and the contents of their intercellular spaces can be taken and then submitted to extraction, providing access to the protein contents.

A sample suitable for the method can also be obtained more directly by "washings" of the skin surface for example using devices of the vane turbine type, or spiral cell type (as described in patent FR 2 667 778) combined with a fluidic circuit, or simply by addition/collection of a drop of buffer on the surface of the skin.

As an illustration of other methods of sampling suitable for application of the invention, we may mention methods using scraping of the upper part of the stratum corneum by means of a twin-blade system. With this technique it is possible to collect scales, which can then be analysed directly by various methods to determine the proportions of minerals, amino acids or lipids. The samples can be stored in a freezer and then analysed by techniques known by a person skilled in the art, such as LC/ESI/MS analysis.

Reference Value

A reference value can be, for example, a content of polypeptide or of nucleic acid sequence determined on a sample of epidermis taken from a skin with normal hydration, and in particular on young skin. Within the scope of the present invention, it was observed that the proportion of polypeptide of the RNase 7 type can decrease physiologically in the skin of subjects over 45 years of age and especially in women.

Therefore "young skin" means the skin of a subject less than about 45 years of age, as opposed to a mature skin.

The RNase 7 values can be expressed in arbitrary units or can be calculated by constructing a calibration curve, based on a recombinant protein or one purified from epidermis. In all cases, the measured proportion of RNase 7 can be expressed relative to the total amount of proteins present in the extract. The total amount of proteins can be measured for example by the Bradford method.

A reference value can be measured in parallel or sequentially to the determination of said content of a polypeptide or of a nucleic acid sequence.

By comparing a content that has been determined against a reference value it is possible to evaluate any deviation relative to this value.

Analysis of the extent and/or nature of this deviation (negative or positive) can provide information on the condition of the epidermis.

For example, determination of a content of polypeptide that is 5 to 10 times lower than a reference value obtained from a normal skin may be indicative of a skin disorder. Conventionally, a normal skin describes a healthy skin that is neither dry, nor greasy.

More particularly, disorders of the skin or of the scalp that can be identified by application of a method of evaluation according to the invention, may be those resulting from deficiency or overexpression of the protein RNase 7, for example those indicated below.

Methods of Determination of the Polypeptide

A polypeptide suitable for application of a method according to the invention can advantageously be the protein RNase 7.

Determination of a content of polypeptide according to the invention or of nucleic acids according to the invention in a sample of epidermis can be carried out by any protocol known by a person skilled in the art.

As a method of detection of a polypeptide, we may mention Western blot, Slot blot, Dot blot, ELISA techniques (Enzyme Linked Immuno-Sorbent Assay) of singleplex or multiplex type, proteomic methods, staining of polypeptides in a polyacrylamide gel with a stain based on silver, with Coomassie Blue or with SYPRO, immunofluorescence, UV absorption, immunohistochemical methods in conventional, electronic or confocal microscopy, FRET (fluorescence resonance energy transfer), TR-FRET methods (time-resolved FRET), FLIM methods (fluorescence lifetime imaging microscopy), FSPIM methods (fluorescence spectral imaging microscopy), FRAP methods (fluorescence recovery after photobleaching), reporter gene methods, AFM methods (atomic force microscopy), plasmonic surface resonance methods, microcalorimetry methods, flow cytometry methods, biosensor methods, radioimmunoassay methods (RIA), methods employing peptide chips, sugar chips, antibody chips, methods of mass spectrometry, methods of spectrometry of the SELDI-TOF type (Ciphergen).

More generally, methods of immunoenzyme assay from solutions of proteins, which are more quantitative and sensitive, can be used in particular. These methods of the ELISA type combine pairs of capture and detection antibodies specific to the target antigen. Commercial antibodies or polyclonal, monoclonal or recombinant antibodies developed specifically can be used. Large-capacity multiplex ELISA techniques can also be employed. Thus, we may mention the multiplex approach of Luminex antibody on beads type (for example Bioplex from Bio-Rad), of the type with antibodies on a flat surface ("antibody arrays") (for example the approach proposed by the company Meso scale Discovery).

In particular, it may be advantageous to detect the presence of a polypeptide according to the invention by means of an antibody, if applicable in a labeled form. Such an antibody can be labeled by means of a substance that is detectable directly or is detectable by reaction with another reagent.

"Antibody" is intended to denote generally monoclonal or polyclonal antibodies, as well as immunoglobulin fragments that are able to bind an antigen and that can be produced by all techniques of genetic engineering known by a person skilled in the art or by enzymatic or chemical cleavage of intact antibodies.

Thus, according to one of its aspects, the present invention also relates to the use of an antibody that binds specifically to a polypeptide according to the invention as a tool for evaluating the condition of the epidermis.

According to one embodiment, an antibody suitable for the invention can bind specifically to a polypeptide represented by the sequence SEQ ID NO 4, or epitopes present in this sequence, or analogs of the latter, notably to an epitope of the amino acid sequence represented by the sequence SEQ ID NO 7, or an analog of the latter.

An antibody that can be used as a tool for evaluating the condition of the epidermis can be obtained by any method known by a person skilled in the art, such as described in "Antibodies: A Laboratory Manual", Cold Spring Harbor Laboratory Press, Cold Spring Harbor, N.Y. (1990).

Thus, according to one of its aspects, the present invention also relates to the use of a recombinant antibody of the monovalent or divalent type which can be obtained by a bacteriophage display method as proposed by the company Antibodies By Design.

Modes of Determination of the Nucleic Acid

A nucleic acid sequence suitable for the application of a method according to the invention can be advantageously a nucleic acid sequence coding for RNase 7, for example of mRNA type.

As examples of methods of detection of nucleic acid sequences, we may mention the chain polymerization reaction (PCR), the reverse-transcriptase chain polymerization reaction (RT-PCR), the quantitative or real-time chain polymerization reaction (Q-PCR), Northern blot, RPA (ribonuclease protection assay), DNA chips, oligonucleotide chips, transcriptomic chips, methods of hybridization in situ.

As an example of agents suitable for the detection of a nucleic acid sequence, and in particular of mRNA, we may mention labeled nucleic acid probes that can hybridize with said sequence.

Said nucleic acid probes can easily be obtained by any method known by a person skilled in the art.

Thus, the nucleic acid sequences according to the invention can be used for making sense and/or antisense oligonucleotide primers, which hybridize with the sequence SEQ ID NO: 1, SEQ ID NO: 2, or SEQ ID NO: 3, or a fragment of the latter or an analog of the latter.

According to another variant embodiment, the present invention relates to a method of assessing a condition of the epidermis comprising at least the steps consisting of:

a) determining a value of the biological activity of a polypeptide according to the invention in a sample of epidermis, and b) comparing said value determined in stage a) against a reference value, Advantageously, the biological activity whose value can be determined can be an enzymatic activity of the ribonuclease type, Any method of measurement of an enzymatic activity known by a person skilled in the art can be employed in a method according to the invention.

For example, it is possible to use a method employing a measurement of the hydrolysis of a fluorescent substrate, specific for a ribonuclease using a preparation of RNase 7 purified from stratum corneum (SC). Measurement of the hydrolysis of said fluorescent substrate is either of the "final point" type or of the "kinetic" type and the enzymatic activity can be referred to the total proteins in the samples.

Methods of Screening According to the Invention

According to another aspect, the present invention relates to the use of a peptide according to the invention or of a nucleic acid sequence coding for said peptide, as a tool for screening biological or chemical compounds or physical treatments that are able to modulate the biological activity and/or the expression of a polypeptide according to the invention and in particular of ribonuclease 7 and/or its interaction with an element of an extracellular matrix.

In the sense of the present invention, the expression "chemical or biological compound or physical treatment capable of or suitable for modulating the biological activity and/or the expression of a polypeptide according to the invention and/or its interaction with an element of an extracellular matrix" means any compound or physical phenomenon capable of or suitable for acting, directly or indirectly, on at least one polypeptide according to the invention, or a nucleic acid sequence coding for the latter, or on an element of an intracellular or extracellular signalling pathway, or of a metabolic pathway involving said polypeptide or on an element of the extracellular matrix, or on an element involved in the regulation of the transcription and/or translation of a nucleic acid sequence coding for said polypeptide.

As an example of physical treatment that may be suitable for the invention, we may mention light radiation, for example UV or IR, notably with an LED (light emitting diode) treatment.

Modulating Agent According to the Invention

Regarding the modulating agents, according to a first embodiment these can comprise a chemical or biological compound able to inhibit the biological activity and/or expression and/or interaction with an element of the extracellular matrix or with another protein of a polypeptide according to the invention.

According to this embodiment, an inhibitor can be selected from a protease, heparin and its derivatives, such as heparan sulphate and peptide fragments able to bind covalently or noncovalently to the active site of a polypeptide of the invention.

The primary amino acid sequence of a polypeptide or of a protein can determine sites specifically recognized by a protease or proteases which, once said sites have been recognized, can induce its cleavage by proteolysis.

Said cleavage can lead to an activation or an inhibition of the biological activity of the polypeptide or of the protein in question.

A so-called inhibiting protease suitable for application of the invention can present a specific site for recognition and/or fixation and cleavage within the amino acid sequence of a polypeptide according to the invention.

Said protease can easily be identified by any enzymatic protocol known by a person skilled in the art.

"Heparin derivative, or alternatively heparan sulphate" means compounds that are derived either from the substitution and/or deletion of a part of the glycosaminoglycans provided that said compounds remain capable of interacting with a polypeptide according to the invention and modulating its biological activity.

For example, for the application of the invention, we may envisage the use of heparans of low molecular weight or heparans of high molecular weight, the manner of preparation of which is well known by a person skilled in the art.

Furthermore, they may be so-called mimetic molecules, i.e. molecules of different chemical structure but nevertheless related to that of a recognized modulating agent, for example a polysaccharide in the case of heparan sulphate and which still have the functions involved in the interaction with the polypeptide.

As an example of compounds or of peptide fragments able to bind covalently or noncovalently to the active site of a polypeptide of the invention, and notably of RNase 7, we may mention the sequence of the signal peptide of RNase 7 represented partly or completely by SEQ ID NO 6 or fragments of the latter possessing a similar function.

According to another embodiment, a biological or chemical modulating agent suitable for the invention can be an activator of the biological activity and/or of the expression of a polypeptide according to the invention and/or an inhibitor of the interaction with an element of the extracellular matrix or a modulator of the interaction with another protein.

As an example of activator suitable for the application of the present invention, we may mention, non-exhaustively, an activator selected from a protease, heparin or a heparin derivative.

An activator can also be a mimetic of RNase 7 capable of or likely to interact with a substrate or a receptor molecule.

As indicated previously the identification of so-called activator proteases suitable for the application is within the routine practice of a person skilled in the art.

According to a first variant, the method of screening according to the invention relates to the characterization of biological or chemical compounds or of physical treatments that are able to modulate the biological activity of a polypeptide according to the invention and comprises at least the steps consisting of a) contacting at least one polypeptide according to the invention, with at least one chemical or biological compound to be tested or treating at least one polypeptide according to the invention physically in conditions favoring manifestation of its biological activity, and b) determining the biological activity of said polypeptide.

"Biological activity" is intended to mean notably with respect to RNase 7, the biological activity of the proprotein (SEQ ID NO 4), of the signal peptide (SEQ ID NO 6), the biological activity of the protein RNase 7 being reflected in an endonuclease activity (SEQ ID NO 5) as well as the immunogenic properties of an epitope identified by the sequence SEQ ID NO 7.

In said method of screening according to the invention, the biological activity of the polypeptide, in particular the ribonuclease activity, can for example be determined by any method known by a person skilled in the art.

According to one embodiment, the biological activity of the polypeptide can be compared against a reference value.

A reference value can be obtained by carrying out a method according to the invention in the absence of any biological or chemical compound to be tested.

According to another embodiment, determination of the property of a chemical or biological compound of modulating the biological activity of a polypeptide according to the invention can also be determined by determining the ability of said compound to modulate the binding of said polypeptide to a substrate.

According to another embodiment, the screening of a biological or chemical compound that is able to modulate the activity of a polypeptide according to the invention can be effected either by measurement of a direct interaction with said polypeptide as indicated previously, or by measurement of the biological activity or the expression of a target molecule belonging to the signaling or metabolic pathways in which said polypeptide may be involved (for example a reporter gene system).

According to a second variant, the method of screening according to the invention is directed toward the characterization of biological or chemical compounds or physical treatments that are able to modulate the interaction of a polypeptide according to the invention with an element of an extracellular matrix and comprises at least the steps consisting of:

a) contacting at least one element of the extracellular matrix, with at least one chemical or biological compound to be tested, or treating said element physically, in conditions favoring an interaction between a polypeptide according to the invention and an element of the extracellular matrix, and b) determining the presence of and/or content of free polypeptide.

The presence of and/or the content of free polypeptide can be compared against a presence of and/or a content of free polypeptide determined after contacting an element of the extracellular matrix with a polypeptide according to the invention in the absence of biological or chemical compounds or of physical treatments to be tested.

Determination of the presence and/or content of free polypeptide can be carried out by methods such as those described previously.

As an example of elements of the extracellular matrix that may be suitable for a method of the invention, we may mention proteoglycan-heparan sulphate complexes, and in particular heparan sulphate.

An element of the extracellular matrix suitable for the invention can be obtained, for example, by taking a sample in vivo or can be obtained from cultures of cells such as fibroblasts or keratinocytes, or from epidermal culture models capable of producing elements of the extracellular matrix.

According to the two variants presented above, the method of screening according to the invention can be carried out on a cellular sample, obtained either from a skin biopsy, from extracts of corneocytes taken with corneodiscs (D-SQUAME®) or by taper striping, or from cells in culture, or an acellular sample, for example a cellular lysate, a preparation of acetone powders from the stratum corneum (SC), from sweat, hair or serum.

For example, we can employ the method of extraction based on acetone powder of SC (Mehul et al., J. Biol Chem., 2000, 275(17):12841-7) to optimize the amount of intercellular proteins from the SC while minimizing the extraction of keratins, which are the predominant matrix proteins of the SC and can limit the identification of other proteins if they are present in excessive amounts in the sample.

The method of identification used is separation of the proteins extracted from the SC by 2D electrophoresis or by 1D electrophoresis followed by the generation of peptides by trypsinolysis and identification of the peptides by LC-MSMS or by generation of peptides by direct trypsinolysis from the protein extracts then separated by cation exchange chromatography or IEF and finally identified by LC-MSMS.

Advantageously, as a cellular sample, we may mention differentiated keratinocytes.

Advantageously, a polypeptide employed in a method according to the present invention can be the protein RNase 7.

According to a third variant, the method of screening according to the invention aims to characterize biological or chemical compounds or physical treatments, capable of modulating the expression of a polypeptide according to the invention, and comprises at least the steps consisting of:

a) contacting at least one nucleic acid sequence coding for a polypeptide according to the invention, with at least one chemical or biological compound to be tested, or treating said sequence physically, in conditions favoring the expression of said sequence, and b) determining the expression of said sequence.

The expression of a nucleic acid sequence can be determined, for example, by means of oligonucleotide probes, by protocols known by a person skilled in the art.

The expression of a nucleic acid sequence according to the invention can be compared against a reference value obtained, for example, by carrying out a method according to the invention in the absence of the test compound.

Composition According to the Invention

According to another of its aspects, the present invention relates to the use of at least one polypeptide according to the invention or of a nucleic acid sequence coding for said polypeptide, or of at least one agent that modulates the expression or the activity of said polypeptide or its interaction with an element of the extracellular matrix for the preparation of a composition intended for the prevention and/or treatment of a disorder of the skin or of the scalp.

In particular, said composition can be cosmetic or therapeutic.

In the sense of the invention, "prevention of a disorder" means reduction of the risk of occurrence of the disorder in question, notably as defined previously.

The amounts of the various constituents of the compositions according to the invention are those used conventionally in the fields in question.

The amount of chemical or biological compound or of polypeptide or of nucleic acid sequence contained in a composition according to the invention, also called "effective amount" depends, of course, on the nature of the compound and on the desired effect and can therefore vary widely.

In the sense of the present invention the expression "effective amount" is intended to mean the minimum amount required for observation of the expected effect, namely a cosmetic effect or a therapeutic effect, it being understood that the effective amounts required for obtaining a cosmetic effect or a therapeutic effect may be identical or different in a particular case.

To state an order of magnitude, a composition can contain a chemical or biological compound or a polypeptide in an amount representing from 0.00001% to 50% of the total weight of the composition, in particular in an amount representing from 0.001% to 10% of the total weight of the composition, and more particularly in an amount representing from 0.1% to 1% of the total weight of the composition.

It is understood that all the compositions considered according to the invention employ a physiologically acceptable medium.

In the sense of the present invention "physiologically acceptable medium" is intended to mean a medium suitable for the application of a composition on a keratinous material, such as the skin, the scalp, the lips, the mucosae and keratin fibres such as the hair, nails and bristles.

In the sense of the present invention "therapeutic" is intended to mean a composition that can be used within the scope of a prophylactic and/or curative treatment, or a method of diagnosis, of a disorder of the skin or of the scalp.

According to a particular embodiment, a composition according to the invention can additionally contain at least one cutaneously active agent.

Actives

As examples of active agents for use within the scope of the present invention, we may mention cosmetic oils, such as silicone oils, vegetable oils of the triglyceride type, hydrocarbon oils such as Parleam oil and the esters of fatty acids and fatty alcohols.

It may also be possible to use actives for improving the condition of the skin, such as hydrating or moisturizing actives or active agents for improving the natural lipid barrier, such as ceramides, cholesterol sulphates and/or fatty acids and mixtures thereof.

It may also be possible to use enzymes having an activity on the skin, such as proteases, lipases, cerebrosidases, amidases and/or melanases and mixtures thereof.

It is also possible to use actives of the microorganism type, notably probiotics, such as those described in applications WO 2006/000992 and WO 2006/037922.

In the sense of the present invention, "probiotic microorganism" means a live microorganism which, when consumed in a suitable amount, has a beneficial effect on the health of its host according to the "Joint FAO/WHO Expert Consultation on Evaluation of Health and Nutritional Properties of Probiotic in Food Including Powder Milk with Live Lactic Acid Bacteria, Oct. 6, 2001", and which can in particular improve the intestinal microbial balance.

Microorganisms suitable for the invention can be selected notably from the Ascomycetes such as *Saccharomyces, Yarrowia, Kluyveromyces, Torulaspora, Schizosaccharomyces pombe, Debaryomyces, Candida, Pichia, Aspergillus* and *Penicillium*, bacteria of the genera *Bifidobacterium, Bacteroides, Fusobacterium, Melissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus* and *Lactobacillus* and mixtures thereof.

As ascomycetes quite particularly suitable for the present invention, we may mention in particular *Yarrowia lipolytica* and *Kluyveromyces lactis*, as well as *Saccharomyces cerevisiae, Torulaspora, Schizosaccharomyces pombe, Candida* and *Pichia*.

Specific examples of probiotic microorganisms are *Bifidobacterium bifidum, Bifidobacterium infantis, Lactobacillus acidophilus, Lactobacillus alimentarius, Lactobacillus curvatus, Lactobacillus delbrueckii* subsp. *Lactis, Lactobacillus gasseri, Lactobacillus johnsonii, Lactobacillus reuteri, Lactobacillus rhamnosus* (*Lactobacillus* GG), *Lactobacillus sake, Lactococcus lactis, Streptococcus thermophilus, Staphylococcus carnosus*, and *Staphylococcus xylosus* and mixtures thereof.

More particularly, they are probiotic microorganisms obtained from the lactic bacteria group, such as notably the *Lactobacillus* species and/or *Bifidobacterium* species. As illustrations of these lactic bacteria, we may mention more particularly *Lactobacillus johnsonii, Lactobacillus reuteri, Lactobacillus rhamnosus, Bifidobacterium bifidum, Bifidobacterium breve, Bifidobacterium animalis, Bifidobacterium lactis, Bifidobacterium longum, Bifidobacterium infantis, Bifidobacterium adolescentis* or *Bifidobacterium pseudocatenulatum* and mixtures thereof.

A strain of *Bifidobacterium lactis* can be obtained from Hansen (Chr. Hansen A/S, 10-12 Boege Alle, P.O. Box 407, DK-2970 Hoersholm, Denmark) under the designation Bb 12.

The microorganism or microorganisms can be included in the composition according to the invention in live, semi-active or inactivated, dead form.

It/they can also be included in the form of fractions of cellular constituents or in the form of metabolites. The microorganism or microorganisms, metabolite or metabolites or fraction or fractions can also be introduced in the form of a lyophilized powder, culture supernatant and/or if applicable in a concentrated form.

In the particular case of topical compositions, it may be advantageous to employ these microorganisms in inactivated, i.e. dead, forms.

With regard to probiotic microorganisms, the following bacterial and yeast genera are generally used:

The lactic bacteria: which produce lactic acid by the fermentation of sugar. They are divided into two groups according to their morphologies:

Lactobacillus species: *acidophilus* (LC1, NCFB 1748); *amylovorus*, *casei* (*Shirota*), *rhamnosus* (GG strain), *brevis*, *crispatus*, *delbrueckii* (subsp *bulgaricus*, *lactis*), *fermentum*, *helveticus*, *gallinarum*, *gasseri*, *johnsonii*, *paracasei*, *plantarum*, *reuteri*, *rhamnosus*, *salivarius*), Cocci: Enterococcus (*faecalis*, *faecium*), Lactococcus lactis (subspp *lactis* or *cremoris*), Leuconostoc mesenteroides subsp *dextranicum*, Pediococcus acidilactici (animal feed), Sporolactobacillus inulinus, Streptococcus salivarius subsp. *Thermophilus*

The bifidobacteria or *Bifidobacterium* species: *Bifidobacterium adolescentis; animalis, bifidum, breve, lactis, longum, infantis*.

The yeasts: *Saccharomyces* (*cerevisiae* or alternatively *boulardii*),

Other sporulated bacteria: Bacillus (*cereus* var *toyo* or *subtilis*), *Bacillus coagulans*, *B. licheniformis*, *Escherichia coli* strain nissle, *Propionibacterium freudenreichii*.

The lactic bacteria and the bifidobacteria are the probiotics used most often.

Specific examples of probiotic microorganisms quite particularly suitable for the invention are *Bifidobacterium bifidum*, *Bifidobacterium infantis*, *Bifidobacterium longum*, *Lactobacillus acidophilus*, *Lactobacillus alimentarius*, *Lactobacillus casei* subsp. *Casei*, *Lactobacillus casei Shirota*, *Lactobacillus paracasei*, *Lactobacillus curvatus*, *Lactobacillus delbrueckii* subsp. *Lactis*, *Lactobacillus gasseri*, *Lactobacillus johnsonii*, *Lactobacillus reuteri*, *Lactobacillus rhamnosus* (*Lactobacillus* GG), *Lactobacillus sake*, *Lactococcus lactis*, *Streptococcus thermophilus*, *Staphylococcus carnosus*, and *Staphylococcus xylosus* and mixtures thereof.

More particularly, they are probiotic microorganisms from the lactic bacteria group, such as notably the *Lactobacillus* and/or the *Bifidobacterium* species. To illustrate these lactic bacteria, we may mention more particularly *Lactobacillus johnsonii*, *Lactobacillus reuteri*, *Lactobacillus rhamnosus*, *Lactobacillus paracasei*, *Lactobacillus casei* or *Bifidobacterium bifidum*, *Bifidobacterium breve*, *Bifidobacterium longum*, *Bifidobacterium animalis*, *Bifidobacterium lactis*, *Bifidobacterium infantis*, *Bifidobacterium adolescentis* or *Bifidobacterium pseudocatenulatum* and mixtures thereof.

Species that are quite particularly suitable are *Lactobacillus johnsonii*, *Lactobacillus paracasei*, *Bifidobacterium adolescentis*, *Bifidobacterium longum* and *Bifidobacterium Lactis* NCC 2818 (also designated Bb12 ATCC 27536) deposited respectively in accordance with the Budapest Treaty with the Institut Pasteur (28 rue du Docteur Roux, F-75024 Paris cedex 15) on Jun. 30, 1992, Jan. 12, 1999, Apr. 15, 1999, Apr. 15, 1999, Jun. 7, 2005 under the following designations CNCM I-1225, CNCM I-2116, CNCM I-2168 and CNCM I-2170 and CNCM I-3446, and the genus *Bifidobacterium longum* (BB536). The strain of *Bifidobacterium lactis* CNCM I-3446 can be obtained from Hansen (Chr. Hansen A/S, 10-12 Boege Alle, P.O. Box 407, DK-2970 Hoersholm, Denmark).

Other examples of active agents suitable for application of the present invention include: analgesic actives, antiyeast actives, antibacterial actives, antiparasitic actives, antifungal actives, antiviral actives, steroidal antiinflammatory actives, anesthetic actives, antipruritic actives, keratolytic actives, anti-free-radical actives, antiseborrheic actives, antidandruff actives, antiacne actives, actives aiming to prevent aging of the skin and/or improve its condition, antidermatitis actives, antiirritant actives, immunomodulating actives, actives for treatment of dry skin, antiperspirant actives, antipsoriatic actives, actives protecting against UV, antihistaminic actives, healing actives, selftanning actives, antioxidants such as green tea or active fractions of the latter, glycerol, Laponite, caffeine, aromatic essential oils, colorants, depigmenting actives, liporegulators, softening, freshening, deodorizing, desensitizing, bleaching, nourishing actives, actives reducing differentiation and/or proliferation and/or skin pigmentation and mixtures thereof.

In particular, among other agents acting on the skin that are suitable for the invention, we may mention hydrating and/or desquamating active agents such as glycol, urea or its derivatives, HEPES, chelating agents, detergents, derivatives of jasmonic acid, and mixture thereof.

Galenical Forms

For administration by the oral route, a composition of the invention can be in any suitable form, in particular in the form of an oral solution, a syrup, a tablet, a coated pill, a capsule or alternatively a foodstuff or a food supplement.

A composition according to the invention can additionally include at least one appropriate excipient suitable for administration by the oral route.

In general, any composition of the invention can be applied on the skin (on any cutaneous area of the body) or on the mucosae (buccal, jugal, gingival, genital, conjunctival, etc.).

As is well known, a cosmetic composition can also contain the additives that are usual in the field of cosmetics, such as hydrophilic or lipophilic gelling agents, hydrophilic or lipophilic additives, preservatives, antioxidants, solvents, perfumes, fillers, filters, odor absorbers and coloring matter.

A polypeptide according to the invention or a nucleic acid sequence coding for said polypeptide, a modulating agent according to the invention or a composition according to the present invention may prove particularly advantageous for improving hydration, the barrier function of the skin, for preventing and/or treating the signs of epidermal aging for example wrinkles, lines, loss of firmness, of elasticity, of density and/or of tonicity of the epidermis.

The cosmetic compositions and/or the polypeptides as defined previously and/or the nucleic acid sequences coding for the latter may thus be particularly suitable as agent for the cosmetic treatment of sensitive skin and/or skin that is dry, very dry or dehydrated, including for the dry zones of mixed skin.

According to another aspect, a polypeptide according to the invention or a nucleic acid sequence coding for said polypeptide can be used for the preparation of a composition intended for the treatment and/or prevention of disorders such as a hyperkeratosis, an ichthyosis, a psoriasis, an atopic dermatitis, an atopy, an eczema, an acne, a lichen, a pruritus, a rosacea, a seborrheic dermatitis, a palmoplantar keratoderma and a prurigo.

The compositions according to the invention can be cosmetic or therapeutic.

In the sense of the invention, a cosmetic composition is a composition intended essentially for achieving an aesthetic effect.

A composition according to the invention can also be used in adjunctive treatment of burns or their sequelae, or for the treatment and/or prevention of skin irritations.

A polypeptide according to the invention or a nucleic acid sequence coding for said polypeptide, or a composition according to the invention can also be used for the purposes of treatment of moderate loss of hair or of bristles and/or stimulation of the growth of the hair or of the bristles.

The skin disorders more particularly addressed by the present invention can be dry skin, very dry skin, and in individuals whose skin has an aged appearance, notably in women over the age of 45 years and/or menopausal, or even elderly, the polypeptides, nucleic sequences, modulating agents and compositions according to the invention may moreover be suitable for the treatment of xeroses and of UV-damaged skin.

In the sense of the present invention, "one" or "a" is to be understood, unless stated otherwise, in the sense of "at least one".

The examples given below are presented as a non-limiting illustration of the invention.

BRIEF DESCRIPTION OF THE DRAWING(S)

FIG. 1 shows a histogram of the average expression of RNase 7 in 4 different types of epidermis (gray column on left: dry aged skin; black column: normal aged skin; white column: dry young skin; gray column on right: normal young skin).

The expression in relative units represents the intensity of the band identified on the Western blot as corresponding to RNase 7, relative to the internal controls.

EXAMPLE

Example I

Evaluation of Expression of Ribonuclease 7 in the Epidermis

Women volunteers in good health with normal skin or dry skin were recruited for the study and were divided into two groups according to age: so-called postmenopausal age (55-60 years) and so-called premenopausal age (35-40 years).

Thus, four groups were obtained: women of so-called postmenopausal age with normal skin (n=13), women of so-called postmenopausal age with dry skin (n=15), women of so-called premenopausal age with normal skin (n=14) and women of so-called premenopausal age with dry skin (n=16).

Samples were taken from the stratum corneum by the so-called "varnish stripping" technique from each of the individuals using a modified protocol of LUNDSTROM and EGELRUD (Acta Denn Venereol, 1991, 71:471).

The "varnish strippings" (tape strippings) were washed with ice-cold acetone and the corneocytes were recovered after filtration and centrifugation.

The soluble proteins were extracted in a PBS-0.1% TX-100 buffer.

Each sample was adjusted to a concentration of 0.15 mg/ml before analysis by Western blot.

10 µg of protein was separated on 4-20% SDS-NuPAGE® gel (INVITROGEN™).

The separated proteins were then transferred to a PDVF membrane (MILLIPORE) using an X-CELL™ blot transfer system (INVITROGEN™) according to the manufacturer's instructions.

The membrane was then saturated with 1% of skimmed milk in TBS-0.05% Tween (TBS-T) for 1 hour at room temperature.

The membrane was then incubated with an antiRNase 7 polyclonal antibody at 1:1000 dilution overnight at 4° C.

The antiRNase 7 polyclonal antibody was obtained by immunization of rabbits with the N-terminal peptide sequence SEQ ID NO 7 of the protein RNase 7.

The antibody obtained was purified with the same peptide as that used for immunizing the rabbits.

The membrane was then washed with the TBS-T buffer and then incubated in the presence of a secondary antirabbit antibody combined with peroxidase for 1 hour at room temperature at 1:4000 dilution.

The membrane was then washed as described previously.

Detection by chemiluminescence was performed with ECL Plus™ blotting reagents (GE HEALTHCARE) according to the manufacturer's instructions.

The images were acquired over a period of one minute by a FLUOR-S® MAX MULTIIMAGER quantitative imaging system (BIORAD).

The intensity of each band was quantified using QUANTITY ONE software (BIORAD).

The data were normalized relative to an amido-black-labeled internal control protein on the same membrane and calculated in the form of the ratio of the intensity of the band of the protein of interest to the intensity of the band of the internal control.

The results shown in FIG. 1 indicate that expression of the protein RNase 7 is strongly diminished in the stratum corneum of dry skin, as well as in the women of so-called postmenopausal age.

The invention claimed is:

1. A method for evaluating a condition of dry epidermis from a sample of epidermis, comprising at least the steps of:
   a) providing an antibody that can bind specifically to an amino acid sequence consisting of SEQ ID NO 7;
   b) determining an amount of at least one polypeptide comprising an amino acid sequence consisting of SEQ ID NO 7 using said antibody from said epidermis sample;
   c) comparing said content determined in step b) against a reference value determined on a sample of epidermis taken from a skin with normal hydration, and
   d) determining a condition of dry epidermis if the amount of said polypeptide is lower than said reference value.

2. The method of claim 1, further includes:
   b) determining an amount of said polypeptide using said antibody in said sample,
   c) comparing said amount determined in step b) against a reference value determined on a sample of epidermis taken from a skin with normal hydration, and
   d) determining a condition of dry epidermis if the amount of said polypeptide is 5 to 10 times lower than said reference value.

* * * * *

SEQUENCE LISTING

```
<160> NUMBER OF SEQ ID NOS: 7

<210> SEQ ID NO 1
<211> LENGTH: 471
<212> TYPE: DNA
<213> ORGANISM: Homo Sapiens

<400> SEQUENCE: 1
atggcaccgg ccagagcagg attctgcccc cttctgctgc ttctgctgct ggggctgtgg      60
gtggcagaga tcccagtcag tgccaagccc aagggcatga cctcatcaca gtggtttaaa     120
attcagcaca tgcagcccag ccctcaagca tgcaactcag ccatgaaaaa cattaacaag     180
cacacaaaac ggtgcaaaga cctcaacacc ttcctgcacg agcctttctc cagtgtggcc     240
```

```
gccacctgcc agaccccaa aatagcctgc aagaatggcg ataaaaactg ccaccagagc      300
cacgggcccg tgtccctgac catgtgtaag ctcacctcag ggaagtatcc gaactgcagg      360
tacaaagaga agcgacagaa caagtcttac gtagtggcct gtaagcctcc ccagaaaaag      420
gactctcagc aattccacct ggttcctgta cacttggaca gagtcctttta g              471
```

<210> SEQ ID NO 2
<211> LENGTH: 387
<212> TYPE: DNA
<213> ORGANISM: Homo Sapiens

<400> SEQUENCE: 2

```
aagcccaagg gcatgaccctc atcacagtgg tttaaaattc agcacatgca gcccagccct      60
caagcatgca actcagccat gaaaaacatt aacaagcaca caaaacggtg caaagacctc      120
aacaccttcc tgcacgagcc tttctccagt gtggccgcca cctgccagac ccccaaaata      180
gcctgcaaga atggcgataa aaactgccac cagagccacg ggcccgtgtc cctgaccatg      240
tgtaagctca cctcagggaa gtatccgaac tgcaggtaca aagagaagcg acagaacaag      300
tcttacgtag tggcctgtaa gcctccccag aaaaaggact ctcagcaatt ccacctggtt      360
cctgtacact tggacagagt cctttag                                          387
```

<210> SEQ ID NO 3
<211> LENGTH: 84
<212> TYPE: DNA
<213> ORGANISM: Homo Sapiens

<400> SEQUENCE: 3

```
atggcaccgg ccagagcagg attctgcccc cttctgctgc ttctgctgct ggggctgtgg      60
gtggcagaga tcccagtcag tgcc                                             84
```

<210> SEQ ID NO 4
<211> LENGTH: 156
<212> TYPE: PRT
<213> ORGANISM: Homo Sapiens

<400> SEQUENCE: 4

```
Met Ala Pro Ala Arg Ala Gly Phe Cys Pro Leu Leu Leu Leu Leu
1               5                   10                  15

Leu Gly Leu Trp Val Ala Glu Ile Pro Val Ser Ala Lys Pro Lys Gly
                20                  25                  30

Met Thr Ser Ser Gln Trp Phe Lys Ile Gln His Met Gln Pro Ser Pro
            35                  40                  45

Gln Ala Cys Asn Ser Ala Met Lys Asn Ile Asn Lys His Thr Lys Arg
        50                  55                  60

Cys Lys Asp Leu Asn Thr Phe Leu His Glu Pro Phe Ser Ser Val Ala
65                  70                  75                  80

Ala Thr Cys Gln Thr Pro Lys Ile Ala Cys Lys Asn Gly Asp Lys Asn
                85                  90                  95

Cys His Gln Ser His Gly Pro Val Ser Leu Thr Met Cys Lys Leu Thr
            100                 105                 110

Ser Gly Lys Tyr Pro Asn Cys Arg Tyr Lys Glu Lys Arg Gln Asn Lys
        115                 120                 125

Ser Tyr Val Val Ala Cys Lys Pro Pro Gln Lys Lys Asp Ser Gln Gln
    130                 135                 140

Phe His Leu Val Pro Val His Leu Asp Arg Val Leu
145                 150                 155
```

```
<210> SEQ ID NO 5
<211> LENGTH: 128
<212> TYPE: PRT
<213> ORGANISM: Homo Sapiens

<400> SEQUENCE: 5

Lys Pro Lys Gly Met Thr Ser Ser Gln Trp Phe Lys Ile Gln His Met
1               5                   10                  15

Gln Pro Ser Pro Gln Ala Cys Asn Ser Ala Met Lys Asn Ile Asn Lys
            20                  25                  30

His Thr Lys Arg Cys Lys Asp Leu Asn Thr Phe Leu His Glu Pro Phe
        35                  40                  45

Ser Ser Val Ala Ala Thr Cys Gln Thr Pro Lys Ile Ala Cys Lys Asn
    50                  55                  60

Gly Asp Lys Asn Cys His Gln Ser His Gly Pro Val Ser Leu Thr Met
65                  70                  75                  80

Cys Lys Leu Thr Ser Gly Lys Tyr Pro Asn Cys Arg Tyr Lys Glu Lys
                85                  90                  95

Arg Gln Asn Lys Ser Tyr Val Val Ala Cys Lys Pro Pro Gln Lys Lys
                100                 105                 110

Asp Ser Gln Gln Phe His Leu Val Pro Val His Leu Asp Arg Val Leu
            115                 120                 125

<210> SEQ ID NO 6
<211> LENGTH: 28
<212> TYPE: PRT
<213> ORGANISM: Homo Sapiens

<400> SEQUENCE: 6

Met Ala Pro Ala Arg Ala Gly Phe Cys Pro Leu Leu Leu Leu Leu Leu
1               5                   10                  15

Leu Gly Leu Trp Val Ala Glu Ile Pro Val Ser Ala
            20                  25

<210> SEQ ID NO 7
<211> LENGTH: 15
<212> TYPE: PRT
<213> ORGANISM: Homo Sapiens

<400> SEQUENCE: 7

Ser Ala Lys Pro Lys Gly Met Thr Ser Ser Gln Trp Phe Lys Ile
1               5                   10                  15
```